United States Patent
Hsieh et al.

(10) Patent No.: US 7,756,312 B2
(45) Date of Patent: Jul. 13, 2010

(54) METHODS AND APPARATUS FOR NOISE ESTIMATION

(75) Inventors: Jiang Hsieh, Brookfield, WI (US); Michael Joseph Washburn, Brookfield, WI (US); Erik Normann Steen, Moss (NO); Gopal B. Avinash, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 937 days.

(21) Appl. No.: 11/551,109

(22) Filed: Oct. 19, 2006

(65) Prior Publication Data

US 2008/0095462 A1 Apr. 24, 2008

(51) Int. Cl.
*G06K 9/00* (2006.01)
*A61B 6/00* (2006.01)

(52) U.S. Cl. .......................... 382/128; 382/275; 378/21

(58) Field of Classification Search ................. 382/100, 382/128, 129, 130, 131, 132, 133, 134, 154, 382/168, 181, 210, 232, 254, 255, 260, 274, 382/275, 276, 291, 305, 312; 600/437; 378/21
See application file for complete search history.

(56) References Cited

U.S. PATENT DOCUMENTS

| 6,885,762 | B2* | 4/2005 | Saha et al. ................ 382/131 |
| 7,187,794 | B2* | 3/2007 | Liang et al. ............... 382/131 |
| 7,272,265 | B2* | 9/2007 | Kouri et al. ............... 382/260 |
| 7,486,811 | B2* | 2/2009 | Kaufman et al. ........... 382/128 |
| 7,529,422 | B2* | 5/2009 | Wang et al. ............... 382/254 |
| 2006/0084869 | A1* | 4/2006 | Kim et al. ................ 600/437 |

OTHER PUBLICATIONS

I Title: Real-Time Speckle Reduction and Coherence Enhancement in Ultrasound Imaging via Nonlinear Anisotropic Diffusion; Article: IEEE Transactions on Biomedical Engineering, vol. 49, No. 9; Author: Abd-Elmoniem et al.; Date: Sep. 2002; pp. 997-1014 (18 pages).*
Title: Real-Time Speckle Reduction and Coherence Enhancement in Ultrasound Imaging via Nonlinear Anisotropic Diffusion; Article: IEEE Transactions on Biomedical Engineering, vol. 49, No. 9; Author: Abd-Elmoniem et al.; Date: Sep. 2002; pp. 997-1014 (18 pages).

* cited by examiner

*Primary Examiner*—Seyed Azarian
(74) *Attorney, Agent, or Firm*—ZPS Group, SC

(57) ABSTRACT

The method includes estimating a noise level in a reconstructed image using a total attenuation of the reconstructed image.

16 Claims, 2 Drawing Sheets

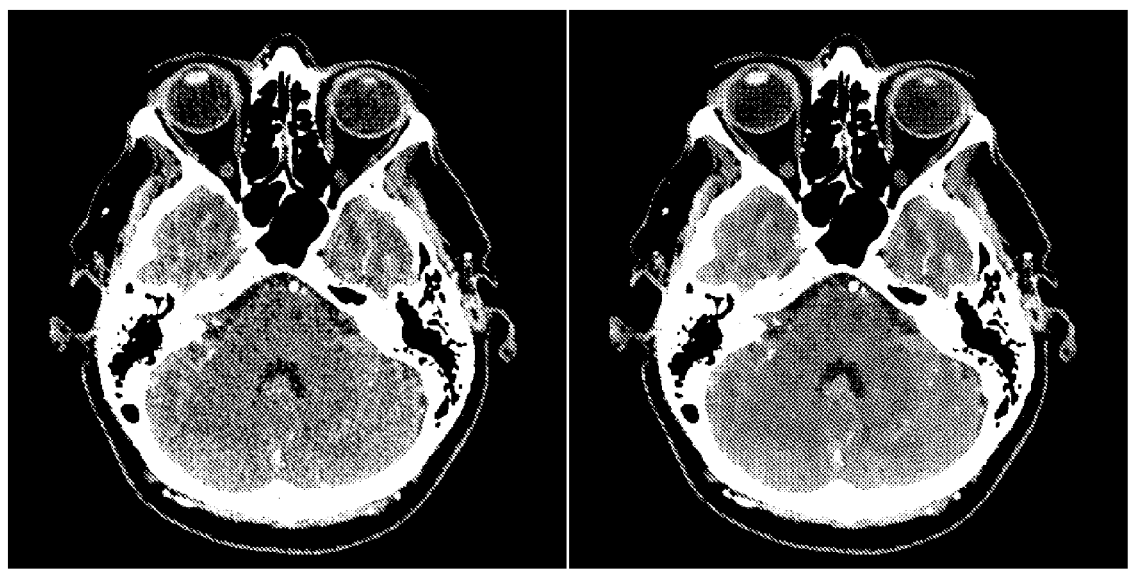
Figure 3 is a patient head scan (left: original image, right: filtered image).

METHODS AND APPARATUS FOR NOISE ESTIMATION

BACKGROUND OF THE INVENTION

This invention relates generally to methods and apparatus for computed tomography (CT), and more particularly to methods and apparatus for noise estimation in CT.

Noise reduction has been the focus of research for x-ray computed tomography (CT) for many years. The goal of noise reduction is not only to improve the visibility of low-contrast objects, but also to reduce the x-ray dose to patients without sacrificing image quality. It is well known that noise reduction can be performed either in the projection space or in the image space. There are pros and cons with either approach. In this patent, we describe an image space filtration approach that significantly improves the noise characteristics of the resulting images.

In recent years, several authors presented reduction methods based on anisotropic diffusion and nonlinear processing of wavelet coefficients. Wavelet based methods can be implemented efficiently. However, traditional wavelet based noise suppression techniques are known to introduce artifacts, such as ringing, near sharp transitions in the image.

Accordingly, an improvement of the original algorithm using a multi-scale version of the anisotropic diffusion is desirable. And using a Dyadic Wavelet scheme to decompose the image into different image scales is also desirable.

BRIEF DESCRIPTION OF THE INVENTION

In one aspect, a method is provided. The method includes estimating a noise level in a reconstructed image using a total attenuation of the reconstructed image.

In another aspect, a computed tomography (CT) system is provided. The system includes a radiation source configured to emit radiation, a detector positioned to receive the radiation, and a computer coupled to the source and the detector. The computer is configured to estimate a noise level in a reconstructed image using a total attenuation of the reconstructed image.

In still another aspect, a computer readable medium is embedded with a program configured to instruct a computer to estimate a noise level in a reconstructed image using a total attenuation of the reconstructed image.

BRIEF DESCRIPTION OF THE DRAWINGS

FIG. 3 is a patient head scan (left: original image, right: filtered image).

DETAILED DESCRIPTION OF THE INVENTION

Figure 1:
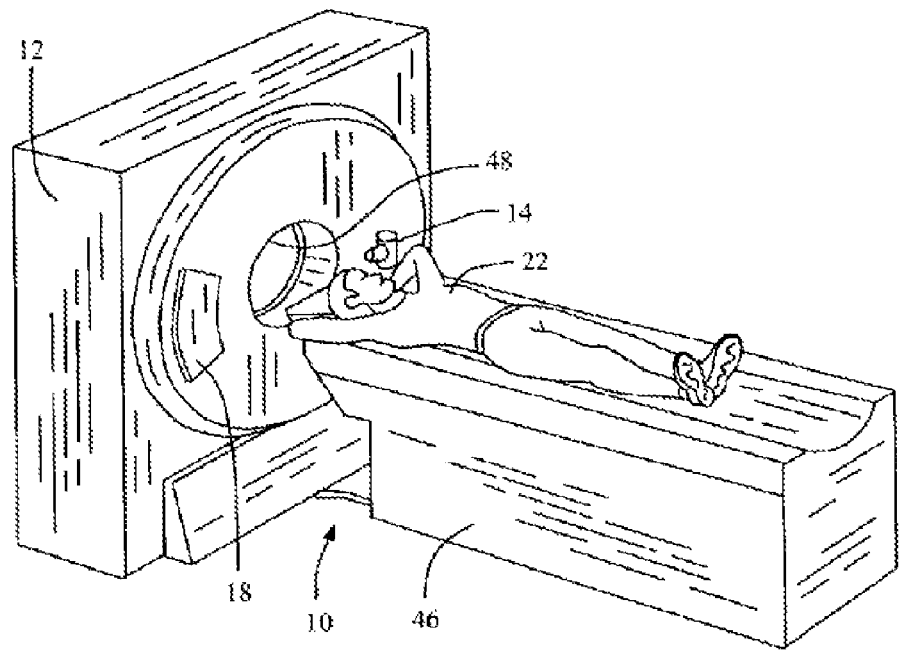
FIG. 1 is a pictorial view of a CT imaging system embodiment.

There are herein provided methods and apparatus useful for any imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

To further reduce the total scan time and produce isotropic spatial resolution, multi-slice CT was developed. In such systems, multiple detector rows are stacked in z such that in each view multiple sets of projections are obtained.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image. Even though an image is described as a 2D viewable image, an image as described herein is understood to include other dimensional images including but not limited to 3D and 4D.

Figure 2:
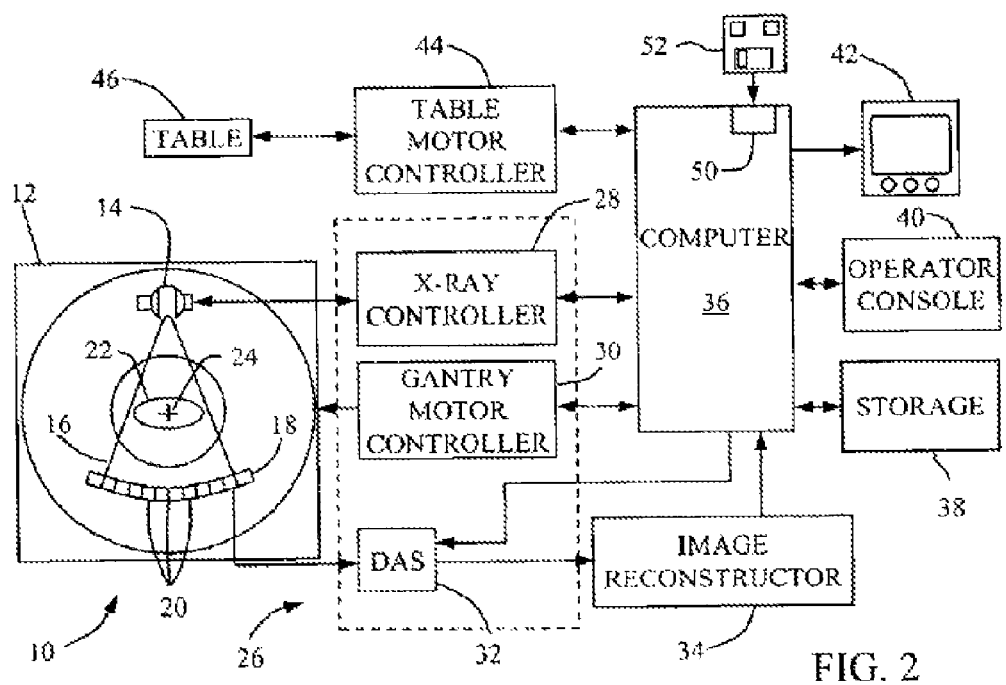
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system.

Gantry 12 has a radiation source 14 that projects a beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center. Additionally, although described in a human patient setting it is contemplated that the benefits of the invention accrue to non-human imaging systems such as those used to image animals.

Returning now to the topic of noise reduction; one of the major obstacles is the estimation of the noise property in the image. To fully understand the problem, a brief discussion on the anisotropic diffusion algorithm is in order. The diffusion equation can be described by the following equation:

$$\frac{\partial I(x, y, t)}{\partial t} = div[d(\|\nabla I\|) \cdot \nabla I] \quad (1)$$

where $\|\nabla I\|$ denotes the local gradient, and $d(\|\nabla I\|)$ the diffusivity function. The function should be monotonically decreasing so that diffusion decreases as the gradient strength increases. One such function is $$d(x) = e^{-\frac{x^2}{2\sigma_n^2}} \quad (2)$$

Note that the parameter $\sigma_n$ is calculated based on the noise of the image. The noise can be either a constant for a particular type of the clinical exam, or the minimum standard deviation measured across the entire image. These approaches, however, do not yield satisfactory results for CT. This is due to the fact that noise changes significantly in CT from slice to slice as a result of the anatomical change. This is particularly problematic for head scans where many highly attenuating bones are present.

To overcome this difficulty, the following method is described. Based on the reconstructed head CT images, the radius (r) of an equivalent water cylinder that has the same total attenuation as the scanned head section can be calculated as:

$$r = \sqrt{\frac{1}{\pi \mu_w}(\iint \mu_{x,y} dxdy)} \quad (3)$$

where $\mu_{x,y}$ is the attenuation coefficient of the head at location (x, y), and $\mu_w$ is the linear attenuation coefficient of water. The relationship between the water phantom size and noise can, for example be established by a set of experiments in which different sizes of water phantoms can be scanned under identical conditions, and the noise in the water phantoms can be measured. In other words, an empirical noise estimation can be made. Alternatively, the phantom size and noise relationship can be determined based on computer simulations. A round water phantom is a simple object to simulate. With a given x-ray tube spectrum and a known bowtie shape, the noise in the round water phantom image can be readily simulated. Yet another method of estimating the noise may use theoretical calculation. Because of the simple phantom shape, an estimation on the projection noise can be calculated. This can then be used to estimate the reconstructed image noise. For a head size between 10 cm to 25 cm in diameter, noise and phantom radius are related by a quadratic function. Based on the fact that variance in the measured phantom scale linearly with the product of x-ray source current and scan speed (other parameters were kept constant), and any difference in different acquisition modes can be accounted for by simple scaling factor based on the number of views and weights used in the reconstruction, the estimated noise in the image, σ, can be expressed as:

$$\sigma^2 = s_{mAs} \cdot s_{mode} \cdot s_{thick} (c_0 + c_1 r + c_2 r^2) \qquad (4)$$

where $s_{mAs}$ is the mAs ratio of the patient scan and the water phantom scans, $s_{mode}$ is the scaling factor to account for different acquisition modes (different helical pitches, and step-and-shoot mode), and $s_{thick}$ is the slice thickness ratio between the patient image and the water phantom images. $c_0$, $c_1$, and $c_2$, are coefficients.

Once the noise value is estimated, the anisotropic diffusion filtering can be carried out. It is known that any noise reduction filter has the potential of reducing the sharpness of the image, due to the low-pass nature of the filtration. To overcome such issues, an enhancement filter is applied after the anisotropic diffusion to sharpen the edges between different anatomical structures. One possible solution is the use of high-pass filters. For example, an un-sharp masking technique can be used in which the slightly smoothed version of the image is subtracted from the original image (after anisotropic diffusion process) to produce edges. The scaled version of the edge is then added to the original image to produce an edge-enhanced image as illustrated in Flowchart 1 below.

Flowchart 1

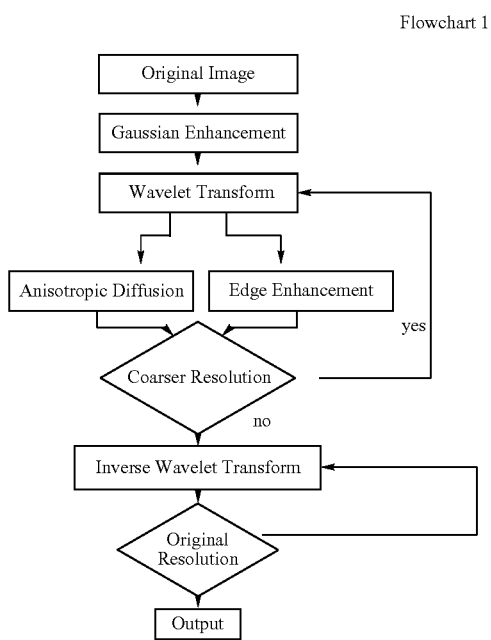

To further improve the computational efficiency of the algorithm, proposed below is an alternative solution. Note that to remove textured noise of different sizes, one can apply the anisotropic diffusion techniques to images at different resolution scales. That is, a speckle noise whose size is larger than a single pixel will not be removed with a 3×3 anisotropic diffusion filter. If the image size is shrunk by a factor of two, the speckle noise size is also reduced by a factor of two. If it becomes a single pixel, the 3×3 filter will work very effectively. The best approach of shrinking down the image size is the application of wavelet transform. In such a transform, three images are generated; one representing the shrink-down version of the original image, and the remaining two representing edges in different directions. One can replace the image-space enhancement convolution with a simple scaling of the wavelet coefficients, since these coefficients represent the edges in the original image at different scales. This process can be repeated for multiple iterations until the desired size of speckle noise is removed. One of the wavelet based enhancement examples is the use of the Harr transform for its computational efficiency. FIG. 3 shows the comparison of the original image and the filtered image of a patient scan. It is clear from the figure that significant improvements in noise can be achieved.

Currently, in the exemplary embodiment, we describe a 2D filter implementation. It should be noted that further improvements could be achieved with a 3D filtering approach to incorporate information across image slices. This is similar to the 2D vs. 3D for other type of image space filtrations. When scans are conducted over time, it is clear that such filtering approach can be applied in 4D where filtration is applied along the temporal domain as well as the spatial domain. It is also clear that such filtering approach can be combined with other types of filters to achieve desired noise textures. Finally, the weighted combination of the filtered image with the original image can be used to arrive at images that are more familiar to domain experts (e.g., radiologists) in terms of their appearance.

Often, radiologists are used to a certain "look" or noise texture in the CT images. They may object to the dramatic change in the appearance of the processed image. To help the radiologists to adjust to the new image, one could add a fraction of the original back into the final image to reduce the impact. The level of enhancement is, therefore, adjustable and can be increased gradually when radiologists get more familiar with the technique. Denoting the unfiltered image by I(x, y) and the filtered image by F(x,y), the final image, I'(x,y), can be obtained with the following formulation:

$$I'(x,y) = \alpha \cdot I(x,y) + (1-\alpha) \cdot F(x,y)$$

Where α is a user adjustable weight between zero and one.

Technical effects of the herein described methods and apparatus include providing significant noise reduction while maintaining clinically relevant information. They (the herein described methods and apparatus) do not cause blurring of structures. They can be used to improve the low-contrast detectability of the image. They can also be used to reduce the x-ray dose to the patient. The empirical noise estimation can be used to adaptively adjust an amount of processing of the reconstructed image. This approach is more robust and computationally more efficient. In addition, the use of the anisotropic diffusion filtering allows significant reduction in noise while maintaining structures in the original image.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A computed tomography (CT) system comprising:
a radiation source configured to emit radiation;
a detector positioned to receive the radiation; and
a computer coupled to the source and the detector, the computer configured to:
access CT image data over a plurality of slices of an object;
reconstruct an image using the CT image data;
determine a total attenuation of the reconstructed image;
estimate noise in the reconstructed image using the determined total attenuation and based on one of a simulation, a theoretical analysis, and data from at least two scanned phantoms; and
apply an anisotropic diffusion algorithm to the reconstructed image based on the estimate of the noise level in the reconstructed image.

2. The system of claim 1 wherein the computer is configured to:
obtain noise data that is empirically measured as a function of a water phantom size; and
estimate the noise in the reconstructed image by scaling the empirically measured noise data using at least one of:
an mAs ratio;
an acquisition mode; and
a slice thickness.

3. The system of claim 1 wherein the computer is configured to estimate the noise based on an empirical measurement and adaptively adjust an amount of processing of the reconstructed image based thereon.

4. The system of claim 1 wherein the computer is configured to shrink at least the reconstructed image to alter a resolution scale of the reconstructed image in order to reduce speckle noise therefrom.

5. The system of claim 4 wherein the computer is configured to shrink at least the reconstructed image by using a wavelet transform.

6. The system of claim 4 wherein the computer is configured to perform multiple iterations of altering the resolution scale until a desired size of speckle noise is removed.

7. A method of CT image processing comprising:
accessing a reconstructed image corresponding to multi-slice image data of an object;
estimating a noise level in the reconstructed image based on a total attenuation of the object, wherein estimating the noise level is based on one of a simulation, a theoretical analysis, and data from at least two scanned phantoms;
anisotropically filtering the reconstructed image using the noise level estimation; and generating a final reconstructed image.

8. The method of claim 7 comprising reconstructing images of different resolutions prior to anisotropically filtering the reconstructed image.

9. The method of claim 7 wherein estimating the noise level comprises empirically estimating the noise by scanning at least two phantoms.

10. The method of claim 9 comprising adaptively adjusting an amount of filtering of the reconstructed image based on the empirical noise estimate.

11. The method of claim 7 comprising performing a wavelet coefficient scaling on the reconstructed image.

12. The method of claim 7 comprising generating a weighted combination of a filtered reconstructed image with the reconstructed image.

13. The method of claim 7 comprising performing multiple iterations of the anisotropical filtering until a desired size of speckle noise is removed.

14. A computer readable storage medium having a computer program stored thereon and representing a set of instructions that when executed by a computer causes the computer to:
estimate an amount of noise in a reconstructed image based on a total attenuation of the reconstructed image and from at least one of;
a simulation;
a theoretical analysis; and
data from at least two scanned phantoms,
apply an anisotropic diffusion filter to the reconstructed image using the estimated amount of noise; and
generate a final reconstructed image.

15. The computer readable storage medium of claim 14 wherein the computer is further caused to iteratively apply the anisotropic diffusion filtering until a desired size of speckle noise is removed.

16. The computer readable storage medium of claim 14 wherein the computer is further caused to apply a wavelet coefficient scaling to the reconstructed image.

* * * * *